United States Patent [19]

Marsella et al.

[11] Patent Number: 5,149,883
[45] Date of Patent: Sep. 22, 1992

[54] PREPARATION OF ALIPHATIC DIHYDROPEROXIDES

[75] Inventors: John A. Marsella; Reinaldo M. Machado, both of Allentown, Pa.

[73] Assignee: Air Products and Chemicals, Inc., Allentown, Pa.

[21] Appl. No.: 699,422

[22] Filed: May 13, 1991

[51] Int. Cl.$^5$ ............................................. C07C 409/04
[52] U.S. Cl. ..................... 568/564; 568/558; 568/561; 568/568
[58] Field of Search ................ 568/564, 568, 558, 561

[56] References Cited

U.S. PATENT DOCUMENTS 3,149,126  9/1964  Milas ..................................... 568/564
3,297,738  1/1967  Mageli et al. ........................ 568/564

FOREIGN PATENT DOCUMENTS 718948  9/1965  Canada ................................ 568/564
936008  5/1960  United Kingdom .

Primary Examiner—Werren B. Lone
Attorney, Agent, or Firm—Russell L. Brewer; James C. Simmons; William F. Marsh

[57] ABSTRACT

This invention relates to an improved process for preparing dihydroperoxyalkanes and, particularly, dimethyldihydroperoxyhexane. The improvement resides in utilizing a tetrahydrofuran derivative which is a liquid as a feedstock. This feedstock then is reacted with hydrogen peroxide in the presence of sulfuric acid to form the dihydroperoxide.

9 Claims, No Drawings

PREPARATION OF ALIPHATIC DIHYDROPEROXIDES

FIELD OF THE INVENTION

This invention relates to an improved process for the preparation of aliphatic dihydroperoxides and particularly dimethyldihydroperoxyhexane.

BACKGROUND OF THE INVENTION

The preparation of aliphatic dihydroperoxides and particularly the dimethyldihydroperoxyhexane derivative is known. It is also known that these dihydroperoxy compounds have utility as polymerization initiators and utility for generating peroxide derivatives thereof.

One general technique for preparing aliphatic dihydroperoxide derivatives has been to react an aliphatic diol with hydrogen peroxide in the presence of a dehydrating acid such as sulfuric acid. The reaction is carried out at relatively low temperature, due to the instability of the dihydroperoxy derivative, at ambient pressures. British Patent 936,008, and particularly Example 1, shows the preparation of 2,5-dimethylhexane-2,5-dihydroperoxide via a conventional route. In that process 2,5-dimethyl-2,5-hexanediol is reacted with hydrogen peroxide in the presence of sulfuric acid. Under vigorous stirring, the temperature of reaction will range from about $-10°$ to $+10°$ C. at atmospheric pressure. The crude dihydroperoxide obtained by the reaction is then washed with unsaturated ammonium sulfate solutions followed by drying. Often the hydrogen peroxide is added to the sulfuric acid-hexane diol mixture or alternatively the hexane diol is added to a mixture of hydrogen peroxide and sulfuric acid.

SUMMARY OF THE INVENTION

This invention relates to an improved process for the preparation of aliphatic dihydroperoxy compounds represented by the formula:

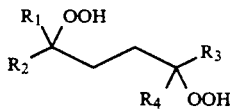

wherein $R_1$, $R_2$, $R_3$ and $R_4$ are independently of one another $C_1$-$C_4$ alkyl groups. The above compounds are formed by reacting a tetrahydrofuran derivative represented by the formula:

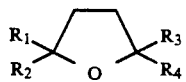

wherein $R_1$, $R_2$, $R_3$ and $R_4$ independently of one another are $C_1$-$C_4$ alkyl and provided further that the compound having a freezing point below $-10°$ C. at atmospheric pressure and a boiling point above $100°$ C.

The tetrahydrofuran derivatives are reacted with hydrogen peroxide in the presence of a dehydrating acid under conditions generating the dihydroperoxy compounds.

There are significant advantages associated with this invention vis-a-vis the prior art technique of forming the dihydroperoxy compounds from the aliphatic diol. For example, the tetrahydrofuran derivatives are liquid under ambient conditions while the diols used in the prior art are solids. Because of the solid nature of the prior art, costly equipment and control measures are required to minimize hazards due to the preparation of the dihydroperoxide compounds. In addition, purification of the solid feedstock is difficult and expensive and impurities may present problems associated with the synthesis or with the use of the dihydroperoxy compounds.

DETAILED DESCRIPTION OF THE INVENTION

This invention relates to an improved process for the preparation of aliphatic dihydroperoxy compounds and particularly to the dimethyldihydroperoxyhexane compounds. The key to the improvement is in the utilization of a tetrahydrofuran which is a liquid under the reaction condition. The tetrahydrofuran typically will have a freezing point below $-10°$ C. and preferably below $-20°$ C. and a boiling point above about $100°$ C. The tetrahydrofuran derivative is represented by the formula:

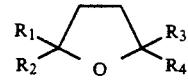

wherein $R_1$, $R_2$, $R_3$ and $R_4$ are independently of one another $C_1$-$C_4$ alkyl groups. Examples of tetrahydrofurans include those compounds where $R_1$ and $R_3$ are ethyl, and $R_2$ and $R_4$ are methyl; $R_1$, $R_2$ and $R_3$ are methyl, and $R_4$ is propyl, and where $R_1$ and $R_3$ are propyl and $R_2$ and $R_4$ are methyl.

The tetrahydrofuran derivatives are reacted with aqueous hydrogen peroxide in water. The molar levels of hydrogen peroxide vis-a-vis the tetrahydrofuran reactant will range from 1 to 10 moles hydrogen peroxide per mole of tetrahydrofuran. When less than about 1 moles of hydrogen peroxide are present per mole of tetrahydrofuran, then yields to the dihydroperoxy compounds are reduced. When molar amounts of hydrogen peroxide per mole of tetrahydrofuran exceed about 10 moles per mole of tetrahydrofuran, no significant advantages are observed and losses of hydrogen peroxide in the process become excessive.

It is known one of the key reactants in the formation of a hydroperoxy compounds is a dehydrating acid of sufficient strength to catalyze the reaction. Conventionally, sulfuric acid having a concentration of from 50% to 90% in water is used, although other acids such as phosphoric can be substituted therefore. In carrying out the process, acid should be at a level sufficient enough to effect reaction between the hydrogen peroxide and the tetrahydrofuran derivative. Typically, this is from 50 to 500% by weight of the tetrahydrofuran. As acid strength increases, or alternatively, the dehydrating effect of the acid increases, there is a greater danger because of an increased explosion hazard. The diluting effect of water present in the hydrogen peroxide and in the dehydrating acid can reduce that explosion hazard, but clearly, critical ranges for hydrogen peroxide and acid should be ascertained.

Although not intending to be bound by theory, the utilization of tetrahydrofuran where the carbon atoms adjacent the ether oxygen are tertiary carbon atoms permit the generation of a carbonium ion. With the cracking of the ring on contact with sulfuric acid, hydrogen peroxide then can add to the carbonium ion generating the dihydroperoxy compounds.

The following examples provided illustrate the preferred embodiment of the invention.

EXAMPLE 1

To 460 grams (6.8 moles) of 50% hydrogen peroxide in water is gradually added, over a period of about 30 minutes, 434 grams of 77% sulfuric acid. The mixture is vigorously stirred and temperature maintained at about 10° C. Then about 88 grams (0.69 moles) of 2,2,5,5-tetramethyltetrahydrofuran are added to the sulfuric acid-hydrogen peroxide mixture. Stirring is continued at 10° C. for about 10 minutes and then the mixture is allowed to warm to room temperature. The reaction is allowed to continue for about an hour at which time it is believed the reaction is complete.

Crude 2,5-dimethylhexane-2,5-dihydroperoxide generated by the reaction is recovered in the conventional manner.

What is claimed is:

1. In a process for the preparation of aliphatic hydroperoxides represented by the formula:

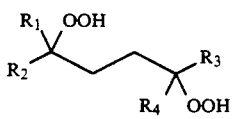

wherein $R_1$, $R_2$, $R_3$, and $R_4$ independently of one another are $C_1$–$C_4$ alkyl, the improvement which comprises reacting a tetrahydrofuran derivative represented by the formula:

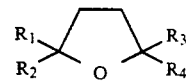

wherein $R_1$, $R_2$, $R_3$, and $R_4$ independently of one another are $C_1$–$C_4$ alkyl, having a freezing point below $-10°$ C. and a boiling point above about 100° C. with hydrogen peroxide and a dehydrating acid selected from the group consisting of sulfuric acid and phosphoric acid to form said dihydroperoxide.

2. The process of claim 1 wherein said tetrahydrofuran is 2,2,5,5-tetramethyltetrahydrofuran.

3. The process of claim 1 wherein the moles of hydrogen peroxide per mole of tetrahydrofuran ranges from 1 to 10 per mole of tetrahydrofuran.

4. The process of claim 3 wherein the dehydrating acid is a sulfuric acid-water mixture, and the concentration of sulfuric acid in water ranges from 50 to 90% by weight.

5. The process of claim 4 wherein reacting of the tetrahydrofuran with hydrogen peroxide and sulfuric acid is carried out at a temperature from $-10°$ to 30° C.

6. The process of claim 5 where the sulfuric acid is present in an amount of from 50 to 500% of the tetrahydrofuran.

7. The process of claim 1 wherein $R_1$ and $R_3$ are ethyl and $R_2$ and $R_4$ are methyl.

8. The process of claim 1 wherein $R_1$, $R_2$ and $R_3$ are methyl and $R_4$ is propyl.

9. The process of claim 1 wherein $R_1$ and $R_3$ are propyl and $R_2$ and $R_4$ are methyl.

* * * * *